(12) United States Patent
Belafsky

(10) Patent No.: US 9,265,489 B2
(45) Date of Patent: Feb. 23, 2016

(54) SWALLOW EXPANSION DEVICE

(75) Inventor: Peter C. Belafsky, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 419 days.

(21) Appl. No.: 13/113,973

(22) Filed: May 23, 2011

(65) Prior Publication Data
US 2011/0288655 A1 Nov. 24, 2011

Related U.S. Application Data

(63) Continuation-in-part of application No. 13/020,752, filed on Feb. 3, 2011, now abandoned, which is a continuation of application No. 11/910,331, filed as application No. PCT/US2006/012726 on Apr. 4, 2006, now Pat. No. 7,882,840.

(60) Provisional application No. 61/347,792, filed on May 24, 2010, provisional application No. 60/668,530, filed on Apr. 4, 2005.

(51) Int. Cl.
| A61F 2/04 | (2013.01) |
| A61B 17/02 | (2006.01) |
| A61B 19/00 | (2006.01) |
| A61B 17/24 | (2006.01) |
| A61B 17/00 | (2006.01) |

(52) U.S. Cl.
CPC ............... *A61B 17/02* (2013.01); *A61B 19/00* (2013.01); *A61B 17/24* (2013.01); *A61B 2017/00876* (2013.01); *A61F 2002/044* (2013.01); *A61F 2210/009* (2013.01)

(58) Field of Classification Search
CPC ............. A61F 2/04; A61F 5/56; A61F 2/203; A61M 16/00
USPC ....................... 128/200.4, 848, 897
See application file for complete search history.

(56) References Cited

U.S. PATENT DOCUMENTS

| 3,926,175 A | 12/1975 | Allen et al. |
| 4,474,181 A | 10/1984 | Schenck |
| 4,511,330 A | 4/1985 | Smilet et al. |
| 5,176,618 A | 1/1993 | Freedman |
| 5,817,000 A | 10/1998 | Souder |
| 5,823,938 A | 10/1998 | Hernandez |
| 6,013,071 A | 1/2000 | Moisdon et al. |

(Continued)

FOREIGN PATENT DOCUMENTS

| WO | 2004-084709 A2 | 10/2004 |
| WO | 2006-108066 A2 | 10/2006 |

OTHER PUBLICATIONS

Belafsky, Peter C., "Manual Control of the Upper Esophageal Sphincter," Laryngoscope, Apr. 2010, vol. 120, issue Supplemental S1, pp. S1-S16.

(Continued)

*Primary Examiner* — Christine H Matthews
(74) *Attorney, Agent, or Firm* — Kilpatrick Townsend & Stockton LLP

(57) ABSTRACT

Methods and devices are disclosed for opening a passageway of a patient. The device includes a base plate for attachment to cricoid cartilage of the patient. A post extends from the base plate through the patient's skin. The post is pulled via a force to manually open the passageway.

13 Claims, 14 Drawing Sheets

(56) References Cited

U.S. PATENT DOCUMENTS

| | | |
|---|---|---|
| 6,234,956 B1 | 5/2001 | He et al. |
| 6,382,815 B1 * | 5/2002 | Klearman et al. ............ 362/253 |
| 6,432,040 B1 | 8/2002 | Meah |
| 7,360,542 B2 | 4/2008 | Nelson et al. |
| 7,445,010 B2 | 11/2008 | Kugler et al. |
| 7,882,840 B2 | 2/2011 | Belafsky et al. |
| 2004/0028676 A1 * | 2/2004 | Klein et al. .................. 424/125 |
| 2004/0034396 A1 | 2/2004 | Freed et al. |
| 2004/0045555 A1 * | 3/2004 | Nelson et al. ................. 128/848 |
| 2004/0049102 A1 | 3/2004 | Nelson et al. |
| 2004/0134491 A1 | 7/2004 | Pflueger et al. |
| 2004/0139975 A1 * | 7/2004 | Nelson et al. ................. 128/848 |
| 2004/0153127 A1 | 8/2004 | Gordon et al. |
| 2004/0181116 A1 | 9/2004 | Kent et al. |
| 2005/0010191 A1 | 1/2005 | Skinner et al. |
| 2005/0126563 A1 * | 6/2005 | van der Burg et al. ... 128/200.24 |
| 2009/0025734 A1 | 1/2009 | Doelling et al. |
| 2011/0213399 A1 | 9/2011 | Belafsky et al. |

OTHER PUBLICATIONS

Yip, Helena T. et al., "Cricopharyngeal myotomy normalizes the opening size of the upper esophageal sphincter in cricopharyngeal dysfunction," Laryngoscope, Jan. 2006, vol. 116, issue 1, pp. 93-96.

International Search Report mailed Sep. 22, 2006, from PCT Application No. PCT/US2006/012726 (8 pages).

International Preliminary Report on Patentability mailed Oct. 9, 2007, from PCT Application No. PCT/US2006/012726 (8 pages).

Extended European Search Report mailed Mar. 2, 2009 from European Application No. 06749373.4 (8 pages).

International Search Report and Written Opinion mailed Jan. 16, 2012, from PCT Application No. PCT/US2011/037794 (14 pages).

International Preliminary Report on Patentability mailed Dec. 6, 2012, from PCT Application No. PCT/US2011/037794 (7 pages).

Examination Report mailed Aug. 1, 2013, from New Zealand Application No. 603742 (2 pages).

Examination Report mailed May 6, 2014, from Australian Application No. 2011258404 (3 pages).

* cited by examiner

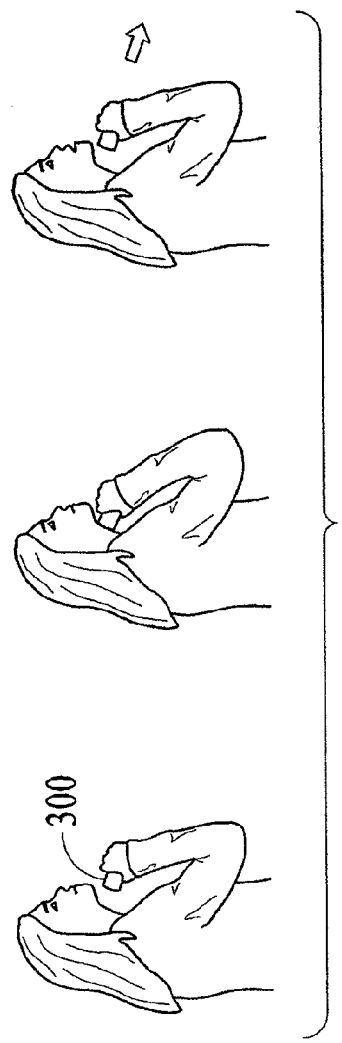
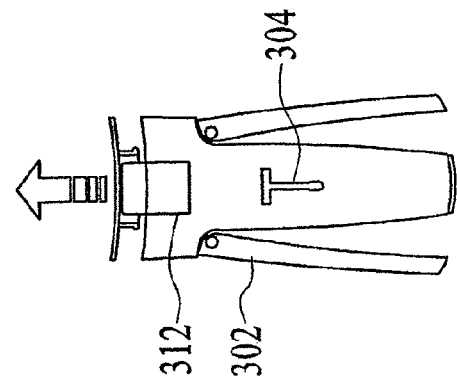
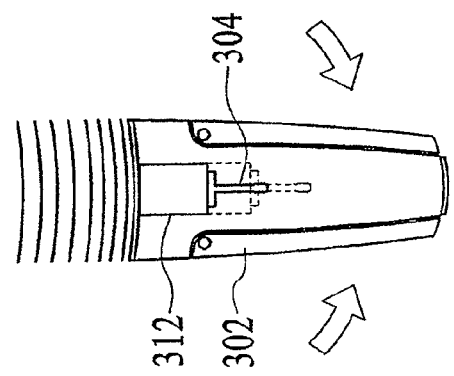
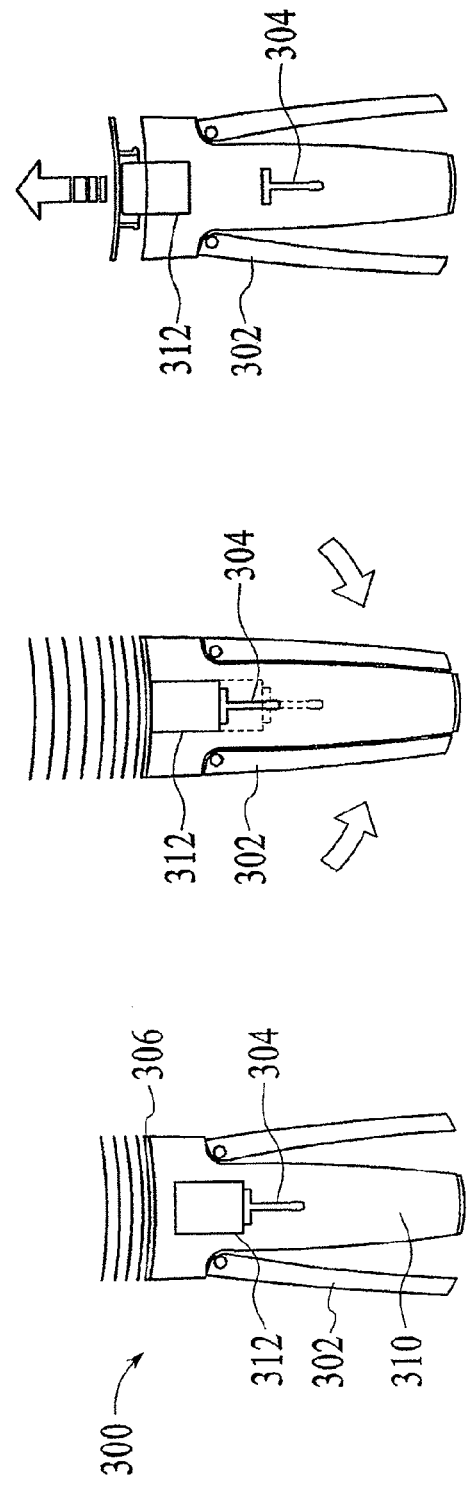
FIG.6
FIG.7A
FIG.7B
FIG.7C

SWALLOW EXPANSION DEVICE

CROSS-REFERENCE TO RELATED APPLICATIONS

This application claims the benefit of U.S. Provisional Application No. 61/347,792, filed May 24, 2010, and is a continuation-in-part of U.S. application Ser. No. 13/020,752, filed on Feb. 3, 2011, which is a continuation of U.S. application Ser. No. 11/910,331, filed Nov. 13, 2008, now U.S. Pat. No. 7,882,840, which is a National Stage of International Application No. PCT/US2006/012726, filed on Apr. 4, 2006, which claims the benefit of U.S. Provisional Application No. 60/668,530, filed Apr. 4, 2005, the entireties of all being incorporated by reference herein.

BACKGROUND OF THE INVENTION

The invention generally concerns manual manipulation of a body passage, and more specifically concerns manual manipulation of an upper sphincter of the esophagus of a patient using an implanted device.

Currently, there are few options for persons with life-threatening, profound oropharyngeal dysphagia (OPD). The most common treatment for persons with profound OPD is non-oral, enteral tube feedings, typically administered by a percutaneous enterogastric tube (PEG). Tube feedings, however, do not prevent the aspiration of a patient's own saliva and are associated with severe alterations in an individual's quality of life. Other options for individuals with profound OPD include separating the airway from the swallowing tube as occurs with total laryngectomy and laryngotracheal separation. These operations are associated with significant morbidity and mortality and eliminate an individual's ability for normal voice production and communication. Because they are so morbid and negatively influence an individual's quality of life, they are seldom chosen by patients.

The three primary functions of the larynx are airway protection, respiration, and phonation. If the larynx is unable to provide adequate airway protection during deglutition or if the pharynx is unable to provide adequate bolus transit through the upper esophageal sphincter, OPD ensues. Causes of OPD include stroke, head and neck cancer, head injury, advancing age, cricopharyngeus muscle dysfunction, amyotrophic lateral sclerosis, pseudobulbar palsy, Alzheimer's disease, Parkinson's disease, multiple sclerosis, muscular dystrophy, and myasthenia gravis.

The impact of OPD on quality of life, morbidity, mortality, and health care expenditure is significant. Complications of dysphagia include aspiration, dehydration, pneumonia, malnutrition, depression, and death. Because of the high economic cost of OPD, the significant impact of OPD on quality of life, and the associated morbidity and mortality, improved recognition and treatment of this disorder are warranted. Despite the high prevalence of dysphagia, current treatment options are limited and millions of people remain disabled and feeding tube dependent.

BRIEF SUMMARY OF THE INVENTION

Embodiments of the invention are directed to methods, systems, and devices that can be used to treat conditions such as dysphagia.

One embodiment of the invention is directed to a method for opening a portion of a passageway of a patient, such as the upper esophageal sphincter or UES, where the patient has a first metallic structure attached to a portion of a patient's neck. The method includes obtaining a second magnetic structure, and placing the second magnetic structure proximate the first metallic structure attached to the portion of the patient's neck. The patient then pulls the second magnetic structure away from the patient's neck to thereby open the passageway (or upper valve or sphincter of the esophagus (UES)).

Another embodiment of the invention is directed to a magnetic device, for use with a first metallic structure implanted in a portion of a patient's neck. The magnetic device includes a handle, and a second magnetic structure, where the second magnetic structure is adapted to attract to the first metallic structure across the skin, and thereby open the upper esophageal sphincter of a patient.

Another embodiment of the invention is directed to a method for opening a passageway in a patient. The method includes placing a structure such as a suture, implant, or a magnetic structure in the patient proximate the passageway, and pulling the structure away from the patient to open the passageway.

Other embodiments of the invention are directed to systems that include the above-described first and second magnetic structures.

Further embodiments of the invention provide a device that mechanically opens the upper sphincter of the esophagus. The device may include a plate and a post. The plate can be attached to the post. The plate may be secured to the cricoid cartilage just below the voice box (larynx) with suture. The post may protrude through the skin. After the device has been implanted, pulling the post forward directly can open the upper esophageal sphincter. This device does not require magnetic components to open the sphincter. The post can be attached to a necklace or can be camouflaged to look like jewelry.

One embodiment of the invention provides a method for opening an upper sphincter of the esophagus of a patient. In the method, a post may be located on a patient, the post having a base surgically secured to cricoid cartilage of the patient's upper sphincter of the esophagus extending through the patient's skin. A force may be applied to the post to effect opening the upper sphincter.

In one aspect of the method, the force is the only action required to open the upper sphincter.

In another aspect of the method, applying the force comprises pulling on a lanyard which is attached to the post.

Another embodiment of the invention provides a device for opening a passageway of a patient. Such a device can include a base plate configured to attach to an anterior ring of the patient's cricoid cartilage. The base plate can articulate with the patient's cricoid cartilage after attachment thereto. A post can extend from the base plate. The post can be of a sufficient length to protrude through a patient's skin when the base plate is attached to the anterior ring of the patient's cricoid cartilage. The post can be further configured with a proximal end to impart a pulling force to the base plate to move the base plate and attached cricoid cartilage, and thereby effect opening of the upper sphincter of the esophagus.

In one aspect of the device, the post comprises a first post portion and a second post portion.

In another aspect of the device, a distal end of the first post portion is affixed to the base plate and a proximal end of the first post portion includes a first means for detachably coupling to the second post portion.

In another aspect of the device, a distal portion of the second post portion comprises a second means for detachably coupling to the first post portion.

In another aspect of the device the base plate is curved to match the profile of the cricoid cartilage of the patient.

In another aspect of the device the proximal end of the post comprises a ring.

In another aspect of the device a lanyard is attached to the ring and further attached to a weight.

In another aspect of the device the base plate comprises a base portion and two lateral wing portions angled towards a posterior direction.

In another aspect of the device the base plate includes a superior edge obtusely angled towards an inferior direction.

In another aspect of the device the base plate includes an inferior edge obtusely angled towards a superior direction.

Another embodiment of the invention provides a method for surgically installing the device into a patient. An incision may be created below the level of the cricoid cartilage of the patient. Strap muscles of the patient may be divided according to a midline. The strap muscles may be moved to expose the cricoid cartilage. The base plate may be attached to the cricoid cartilage with sutures. In some embodiments, screws and/or clips can be used in lieu of or in conjunction with the sutures. The post may be positioned to extend outside of the skin of the patient. The divided strap muscles may be repositioned about the midline. The incision may then be closed.

Another embodiment of the invention provides that one or more aspects from any embodiment may be combined with one or more aspects of any other embodiment without departing from the scope of the invention.

These and other embodiments of the invention are described in further detail below with reference to the following figures.

BRIEF DESCRIPTION OF THE DRAWINGS

FIG. 6 shows various images of a person using a magnetic device according to an embodiment of the invention.

FIGS. 7A-7C show schematic side views of a magnetic device, wherein the second magnetic structure in the magnetic device is in different positions.

DETAILED DESCRIPTION OF THE INVENTION

Magnetic Devices:

To address the above problems, a device such as a magnet, suture, or the like may be placed adjacent to a passageway (e.g., the upper esophageal sphincter) in a patient. The device can be pulled by the patient away from the patient to open the swallowing passageway. Embodiments of the invention would give people back the precious gift of swallowing.

Preferred embodiments of the invention use magnetic structures to open a patient's passageway. As used herein, the term "magnetic material" includes materials that are capable of being magnetized or capable of being attracted to a magnet. The magnetic structures can attract each other across the skin and would serve to pull the cricopharyngeous (upper valve of the esophagus) open, thereby allowing persons with oropharyngeal dysphagia to swallow. In embodiments of the invention, a first metallic, or first magnetic structure (which may be, for example, paramagnetic or ferromagnetic) can be placed under the skin through a minimally invasive procedure that can be performed under local anesthesia. Once the skin heals, an external second magnetic structure (which may also be, for example, paramagnetic or ferromagnetic) can attract the implanted first magnetic structure across the cervical skin. Traction on the second, external magnetic structure pulls the upper valve of the esophagus open and allows food to pass. In some cases, the second magnetic structure may be referred to as a "swallow magnet" or "swallow device".

Placing magnets and other metals in the body has precedent in medicine. Head and neck surgeons place metal plates in the body to repair facial fractures on a daily basis. Cochlear implants utilize magnets to affix transmitters to receivers across the skin. Magnets have been placed in the eyelid to close the eye of persons with facial paralysis. The inventive swallow expansion device provides for a novel treatment for swallowing disorders. Given the millions of individuals with oropharyngeal dysphagia, the potential of this invention is limitless. Embodiments of the invention are inexpensive to develop, and are technically easy to place under the skin. If any problems develop, the implanted magnetic structure can be easily removed or replaced.

Figure 1:
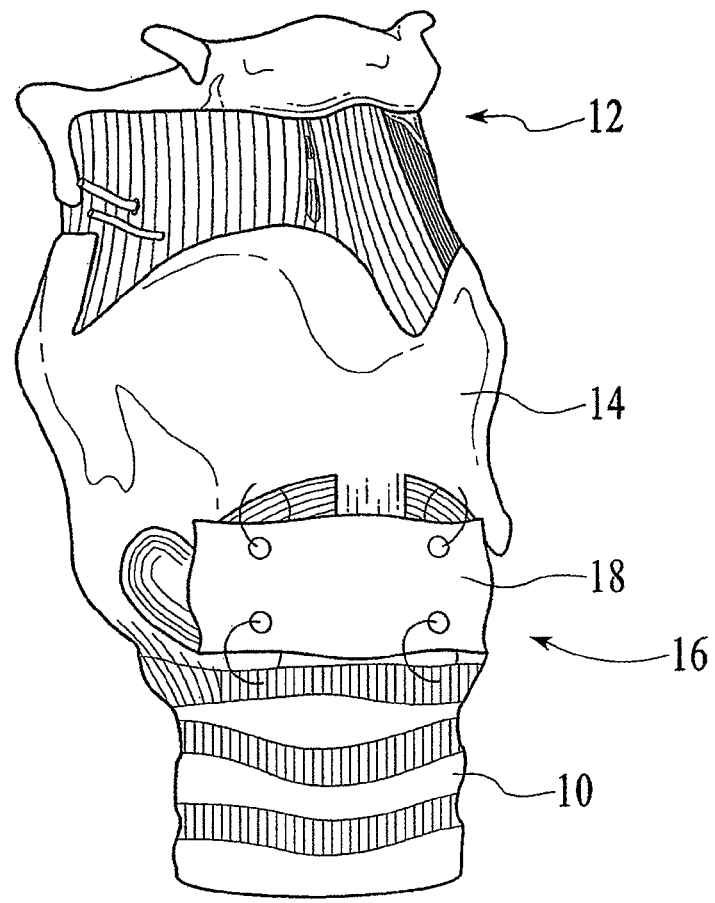
FIG. 1 shows a diagram of portions of a patient's throat with a first magnetic (or metallic) structure attached to the cricoid and thyroid cartilages.

FIG. 1 shows some portions of a patient's neck including a hyoid bone 12, thyroid cartilage 14, cricoid cartilage 16, and the trachea 10. In embodiments of the invention, an internal first magnetic structure 16 is secured to the cricoid and thyroid cartilages through a small skin incision. This can be done with local anesthesia and would only be considered a minimally invasive procedure. The skin would then be closed over the first magnetic structure and would then be allowed to heal.

The internal first magnetic structure 16 may be in any form and may include any suitable material. As noted below, it may be part of a more complex implant assembly. It may have a rectangular or circular shape, and may include any suitable magnetic material (e.g., Fe, Fe—Co, Ni, electrical steel, etc.). The first magnetic structure 16 may alternatively or additionally include a number of holes or attachment points for sutures (or some other attachment mechanism) so that the internal magnet can be secured to cricoid and thyroid cartilages. The first magnetic structure 16 may also be coated with a biocompatible material such as titanium so that it may be rendered implantable.

Figure 2:
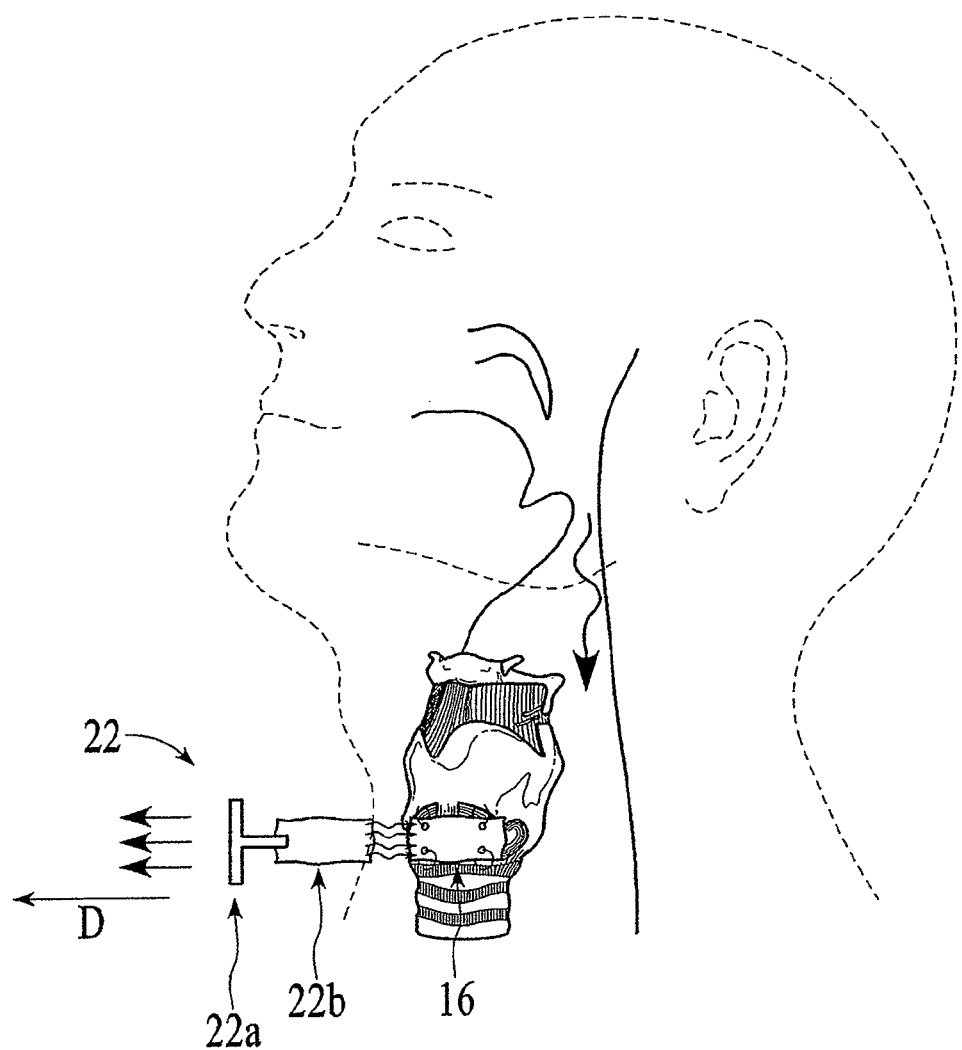
FIG. 2 shows a system including a first magnetic (or metallic) structure and second magnetic structure, as it would be used by a patient.

As shown in FIG. 2, a second magnetic structure 22(b) can be attached to a handle 22(a) in the form of a T-bar. The handle 22(a) and the second magnetic structure 22(b) may form a magnetic device 22. The second magnetic structure 22(b) is external to the patient, and would be used to attract the first magnetic structure 16 through the skin during meals. The first magnetic structure 16 is under the skin. Gentle anterior traction on the magnetic structures is achieved by pulling on the handle 22(b) in the direction D, thereby opening the upper sphincter (cricopharyngeal muscle) of the esophagus, allowing food to pass and allowing the patient to eat. The second magnetic structure 22(b) can be removed after the meal.

Like the first magnetic structure 16, the second magnetic structure 22(b) may be in any suitable form and may comprise any suitable magnetic material.

Figure 3A:
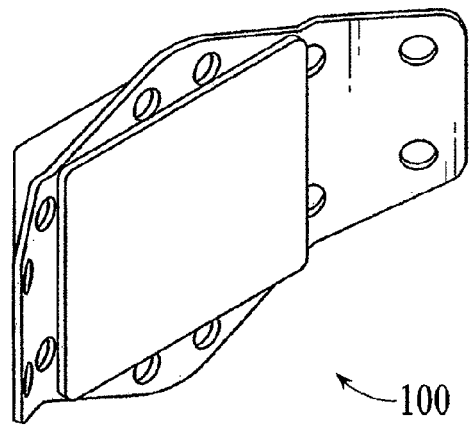
FIG. 3A shows a perspective, exploded view of an implant assembly according to an embodiment of the invention.
Figure 3B:
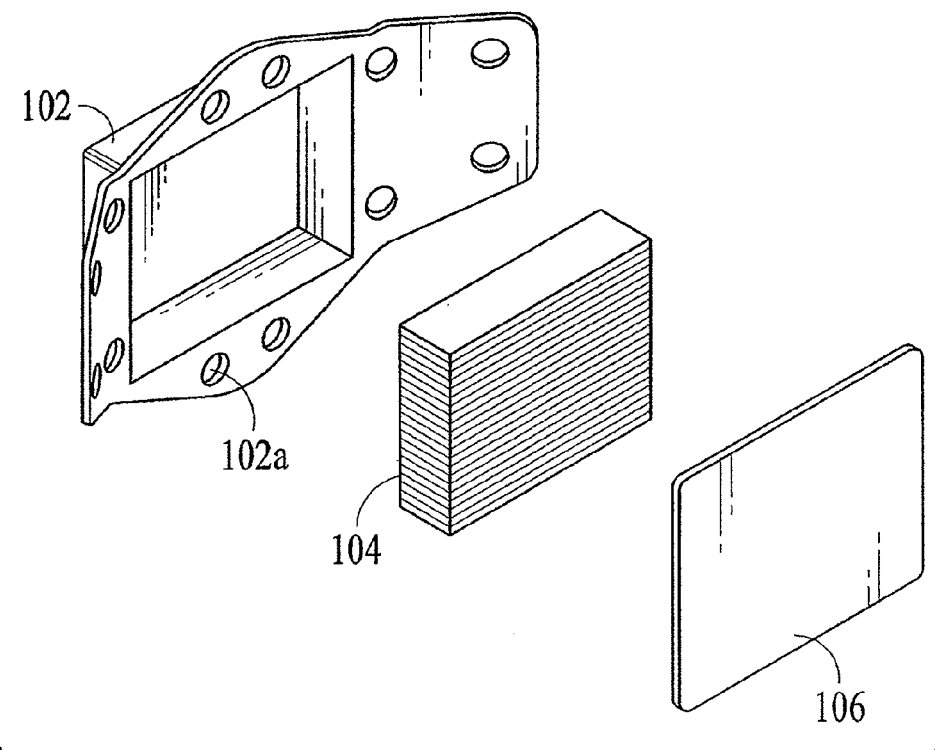
FIG. 3B shows a perspective view of the implant assembly shown in FIG. 3(a), in an assembled state.

FIG. 3A shows a perspective view of an implant assembly 100 according to an embodiment of the invention. As shown in FIG. 3B, the implant assembly 100 includes a second magnetic structure 104, which is sandwiched between a titanium cup-shaped structure 102 and a titanium plate 106. The titanium cup shaped structure may include a number of holes 102(a) around a flange portion of the cup shaped structure 102. Sutures or other connecting structures may be used to secure the implant assembly 100 to a patient's cricoid. The titanium plate 106 may be welded or otherwise attached to the cup-shaped structure 102 to enclose the second magnetic structure 104.

Figure 4:
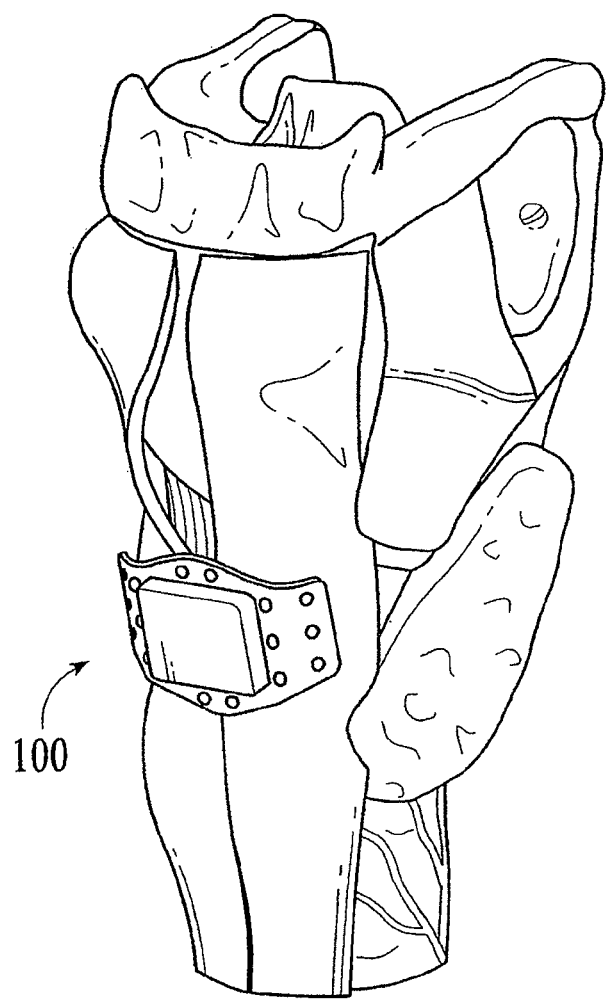
FIG. 4 shows a perspective view of the implant assembly shown in FIG. 3(b) as it would be attached to the cricoid and thyroid cartilages in a patient.

FIG. 4 shows how the implant assembly 100 that is shown in FIGS. 3A and 3B would be attached to a patient's cricoid.

Figure 5:
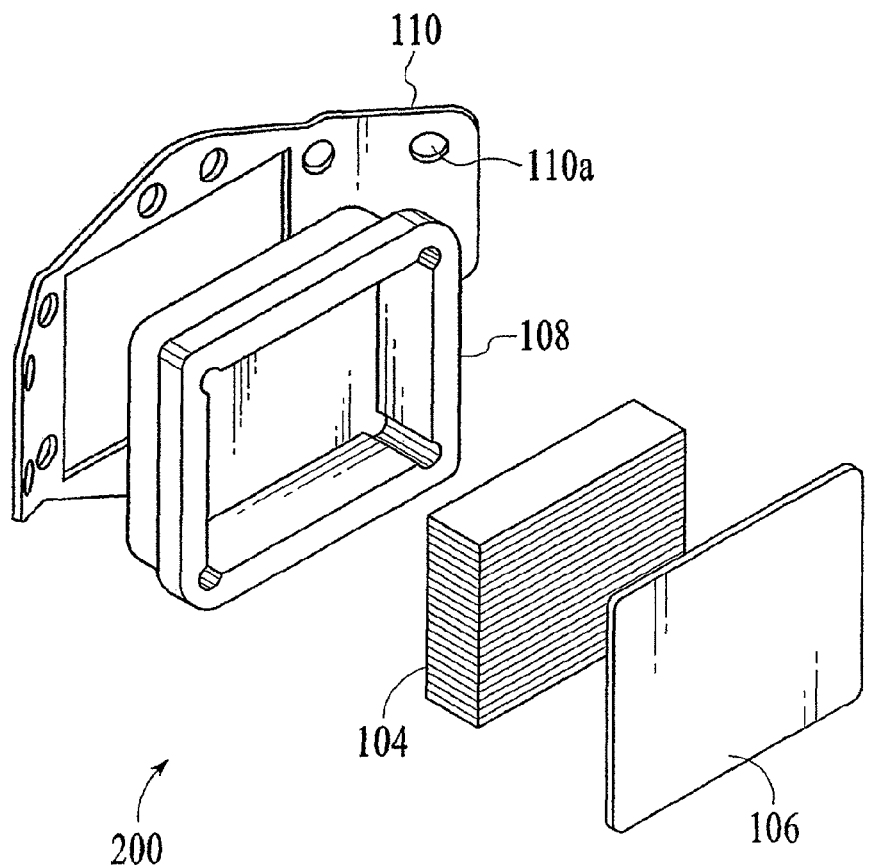
FIG. 5 shows a perspective view of another implant assembly embodiment. In this example, the implant assembly has a separate flange structure and a separate cup-shaped structure.

FIG. 5 shows another implant assembly 200 embodiment. In this embodiment, a flange structure 110 including holes 110A has a central aperture that receives a cup shaped structure 108 that has a peripheral flange. As in the implant assembly embodiment shown in FIG. 3A and FIG. 3A, in the implant assembly 200 shown in FIG. 5, the second magnetic structure 104 is sandwiched between the cup shaped structure 108 and a titanium plate 106. The flange structure 110, the cup shaped structure 108, and the titanium plate 106 may be welded together.

Although titanium plates, cup-shaped structures, and flange structures are discussed in these examples, it is understood that the implant assemblies according to embodiments may include any number of additional components and may include any suitable type of biocompatible material.

FIG. 6 shows how a magnetic device according to an embodiment of the invention would be used. As shown in FIG. 6, a patient obtains and then places a magnetic device 300 including a second magnetic structure close to her neck and then pulls the magnetic device 300 away from her neck. The second magnetic structure (not shown) in the magnetic device 300 pulls the first magnetic device (not shown) implanted in the patient's neck. This pulls on the patient's cricopharyngeous muscle and opens the cervical esophagus, thereby allowing the patient to swallow.

FIG. 7A shows a magnetic device 300 including first and second handles 302, which are pivotably attached to a housing 310. A curved pad 306 is at the front portion of the device 300 and is intended to conform to the outer surface of a patient's neck. A pushing element 304 is attached to a second magnetic structure 312, and both of these components are in the housing 310. The second magnetic structure 312 is recessed in the housing 310 until the patient squeezes the handles 302. Minimal magnetic attraction between the interacting first and second magnetic structures allows comfortable placement and removal of the magnetic device 300.

FIG. 7B shows the magnetic device 300 when the user squeezes the handles 302. After squeezing the handles 302, the second magnetic structure 104 moves toward the front of the magnetic device 300 and magnetically engages a first magnetic structure that is implanted in the patient.

FIG. 7C shows the magnetic device 300 after the patient releases the handles 302. To avoid any damage to the cricoid, the magnetic device 300 may include an automatic release mechanism, which releases the second magnetic structure in the magnetic device 300 if the pulling force exceeds safe parameters (e.g., 7-10 lbs. of force).

The magnetic device 300 includes handles that control how much magnetic attraction is available to pull an internal implant forward in order to open the upper esophageal sphincter. Thin patients need less magnetic power than persons with thicker necks. The device can be adjusted to provide variable amounts of magnetic attraction.

Figure 8A:
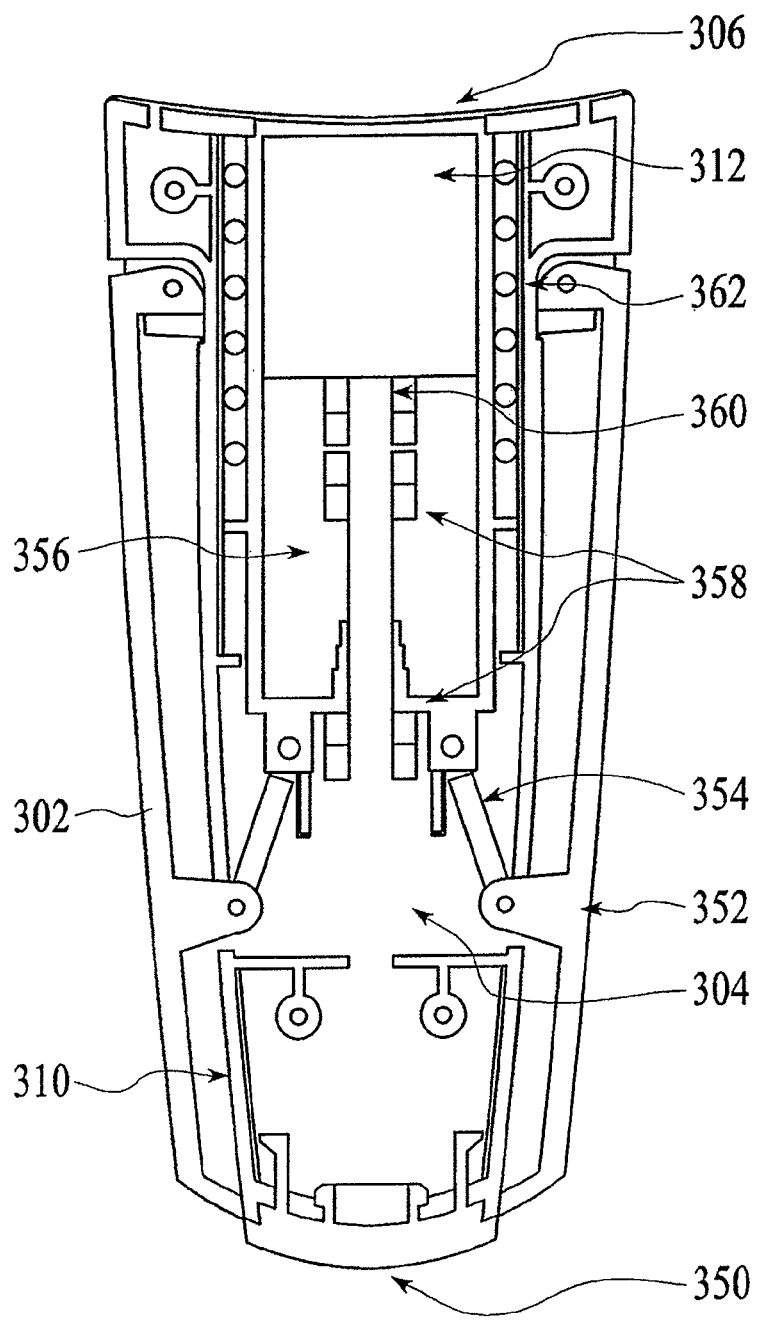
FIG. 8A shows a side, cross-sectional view of a magnetic device with a retractable second magnetic structure. The magnetic device shown in FIG. 8(a) is at full magnetic power.

FIG. 8A shows a side, cross-sectional view of a magnetic device 300 according to an embodiment of the invention. A front portion of the device 300 includes a silicone pad 306 for skin protection. A second magnetic structure 312 is shown as being adjacent to the silicone pad 306, and is in a "full magnetic power" position. A spring 362 biases the second magnetic structure 312 rearward, in the absence of pressure on the handles 302. Linking structures 354 pivotably link the handles 302 and a cylindrical structure 356 holding the second magnetic structure 312, so that the inward depression of the handles 302 cause the second magnetic structure 312 to move toward the front of the magnetic device 300. A cap 350 is provided at the rear of the magnetic device 300 in order to hide the internal components (e.g., the power adjust mechanism) of the magnetic device. The cap 350 may be attached to a housing 310, which houses components such as the cylindrical structure 356, the second magnetic structure 312, the spring 362, and the linking structure 354.

A threaded screw structure 304 and a number of stops 358 may also be provided in the magnetic device 300. These components may be used to adjust the position of the second magnetic structure 312 within the magnetic device 300 so that the magnetic power of the magnetic device 300 can be correspondingly adjusted by a patient.

As shown in FIG. 8A, the second magnetic structure 312 can be positioned anywhere within the magnetic device 300 so that the magnetic power of the magnetic device 300 can be adjusted to a desired level.

Figure 8B:
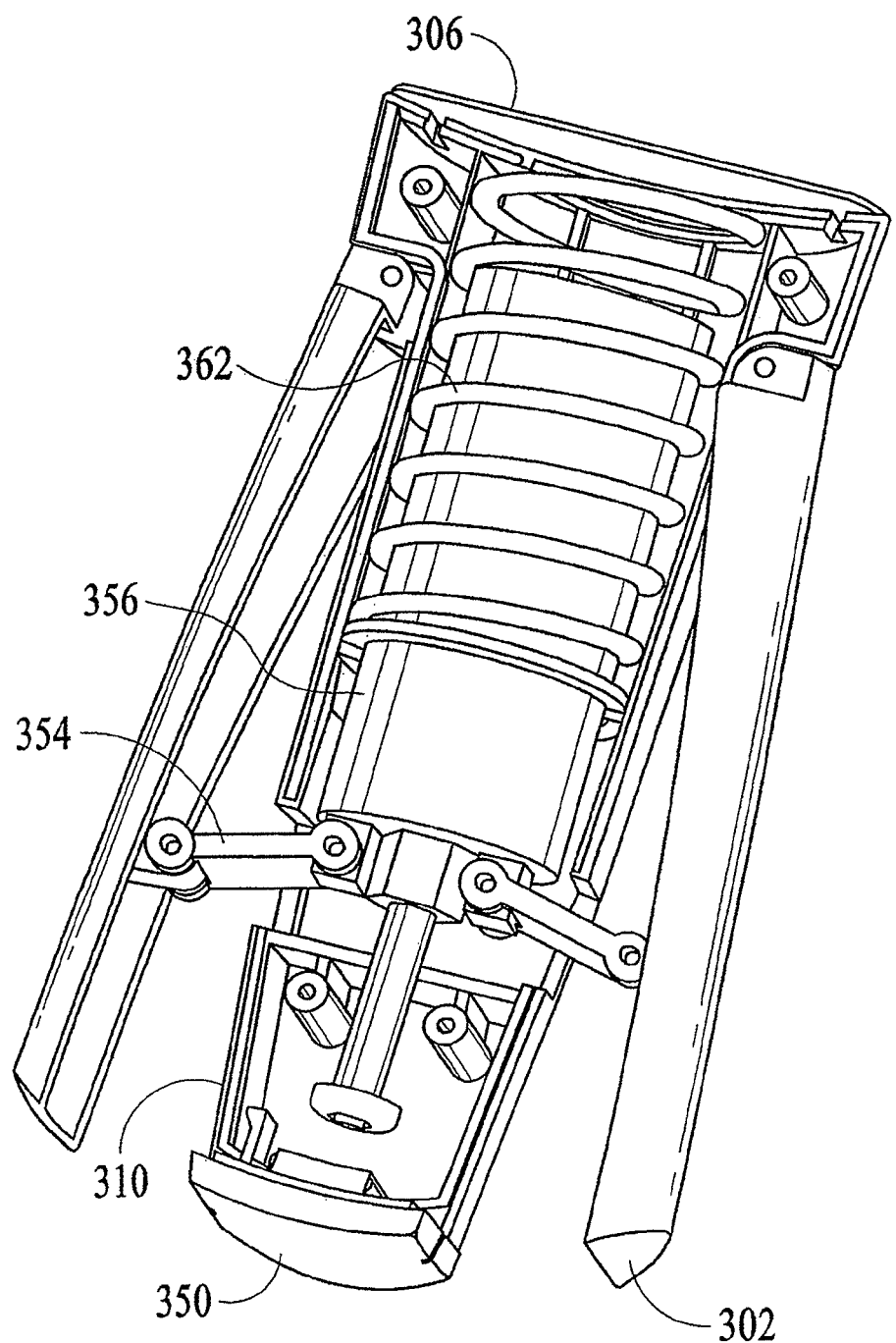
FIG. 8B shows a side, cross-sectional view of a magnetic device of the type shown in FIG. 8(a). The magnetic device is not at full power and a second magnetic structure that is inside of a cylindrical structure is in a partially retracted position.

FIG. 8B shows a side, cross-sectional view of a magnetic device of the type shown in FIG. 8B. In FIG. 8B, like numerals designate like elements as in FIG. 8B). The magnetic device is not at full power and a second magnetic structure that is inside of a cylindrical structure is in a partially retracted position. The handles 302 project outward when the second magnetic structure is in a retracted position.

As described above, preferred embodiments of the invention use magnetic structures and magnetic devices to open a patient's passageway. However, in other embodiments, magnetic structures and devices are not needed. For example, in one embodiment of the invention, a structure such as a suture can placed around the cricoid cartilage in individuals with oropharyngeal dysphagia. When the suture is pulled forward, the cricopharyngeous (CP) muscle pulls forward and opens up the cervical esophagus. A handle or other structure may be coupled to the suture to help the patient pull the suture forward. Patients who were previously unable to swallow are able to eat with this simple suture in place. The suture goes through the skin and stays in place. The suture could be susceptible to infection so appropriate measures can be taken to reduce the risk of infection. For example, the suture may be coated with a biocompatible material which would reduce the risk of infection.

Figure 9:
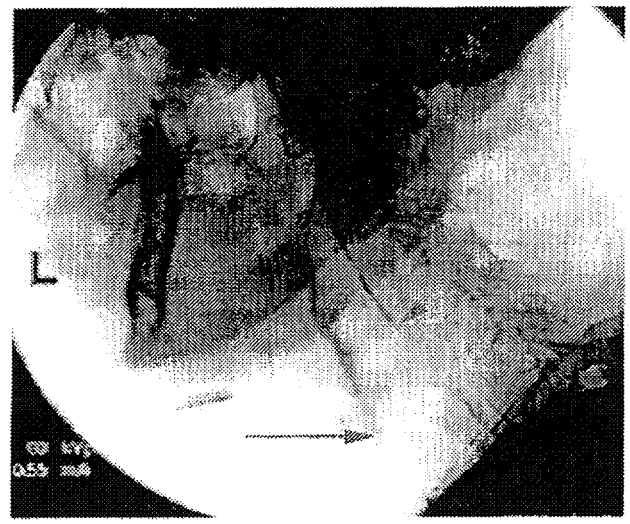
FIGS. 9-10 show two images from a fluoroscopic swallow evaluation before and after pulling on a cricoid structure.
Figure 10:
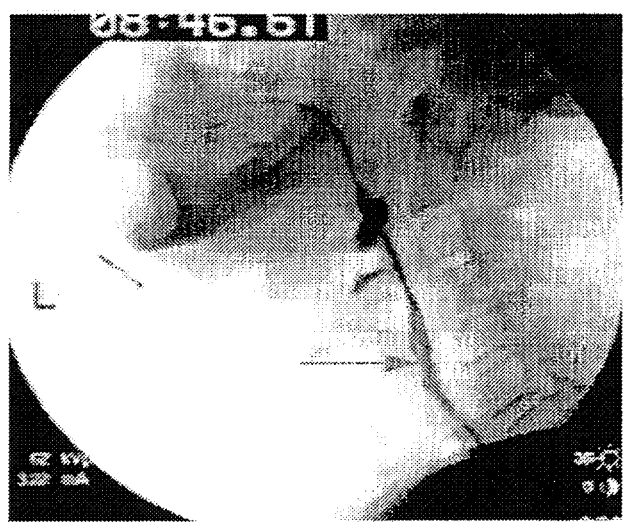

FIGS. 9-10 show two images from a fluoroscopic swallow evaluation before and after pulling on a cricoid suture. In FIG. 9, the patient aspirated without traction on the suture and was not able to pass any food into his esophagus. The upper esophageal sphincter (UES) does not open causing the barium column to impede (arrowhead). Because the UES does not open, the food has nowhere to go but into the trachea, resulting in aspiration. Barium can be seen crossing the vocal folds into the proximal trachea (arrow).

Referring to FIG. 10, with traction on the suture, the patient was able to pass food safely into his esophagus without any aspiration. In FIG. 10, the same patient as in FIG. 9 is placing anterior traction on a suture placed around the cricoid cartilage during the swallow. The UES is now open and the barium passes easily into the esophagus without any aspiration (arrow). The embodiments of the invention that use the magnetic structures can provide more anterior traction than the simple suture and the improvement in swallowing should be even more dramatic.

Although the use of a cricoid suture is acceptable, as noted above, preferred embodiments of the invention use an implanted magnetic structure that is secured to the cricoid cartilage. Because the magnetic structure in the preferred invention embodiments is secured directly to the cricoid, it will provide better anterior traction to open the upper sphincter of the esophagus than a lone suture and the improvement in swallowing should be even greater than using a long suture as a means for opening the esophagus. Also, because the magnetic structure is implanted under the skin, it will not serve as a source for infection. Thus, the embodiments of the invention that use magnetic devices and magnetic structures to open a patient's passageway have a number of advantages over embodiments using sutures as a traction mechanism.

Post Devices:

Magnetic devices, such as discussed above, and by the instant inventor in *Manual Control of the Upper Esophageal Sphincter*, The Laryngoscope 120 (April 2010), which is incorporated by reference herein, utilize magnetic force to move an implanted device to open the upper sphincter of the esophagus. Such magnetic devices are useful, however, not all patients desire these implants. Further, a portion of patients are in such poor condition that a post-implantation MRI would be expected, which would be incompatible with a magnetic material. Accordingly, many patients require a device that is MR compatible and/or MR safe.

A device is disclosed in one embodiment which comprises a plate that is attached to a post. The plate and post are both made of non-magnetic material, such as titanium. The plate is specifically shaped to articulate with the anterior ring of the cricoid cartilage. The plate is secured to the cricoid cartilage with sutures. The post pierces the skin over the cricoid cartilage. A ring screws onto a sharp piercing of the post. The purpose of the ring is to protect the patient from the sharp piercing. It may also be used to attach to a necklace or to a piece of other jewelry to conceal the piercing or to assist with pulling the post forward. Pulling the post forward, pulls the cricoid cartilage forward and directly opens the upper sphincter of the esophagus. This will allow a patient to drink and swallow. The device can be made entirely of titanium and does not require an iron core or an external actuation inducing magnetic device.

Figure 11A:
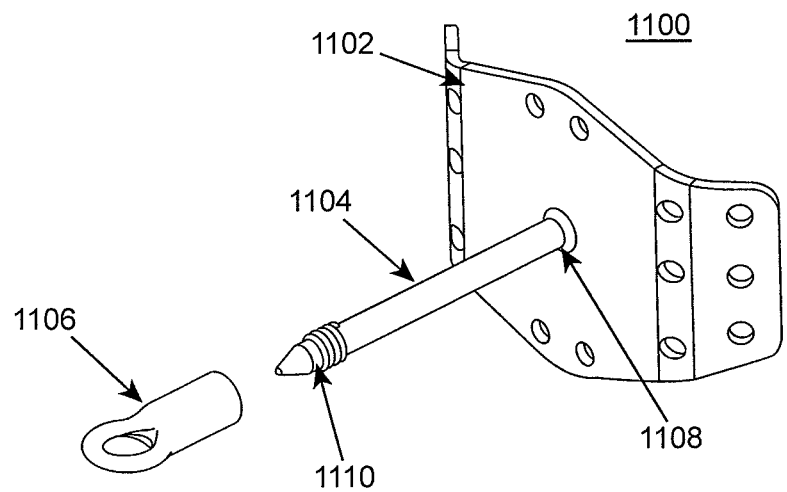
FIGS. 11A and 11B respectfully show exploded and assembled perspective views of a device for opening an upper sphincter of the esophagus of a patient, according to an embodiment of the invention.
Figure 11B:
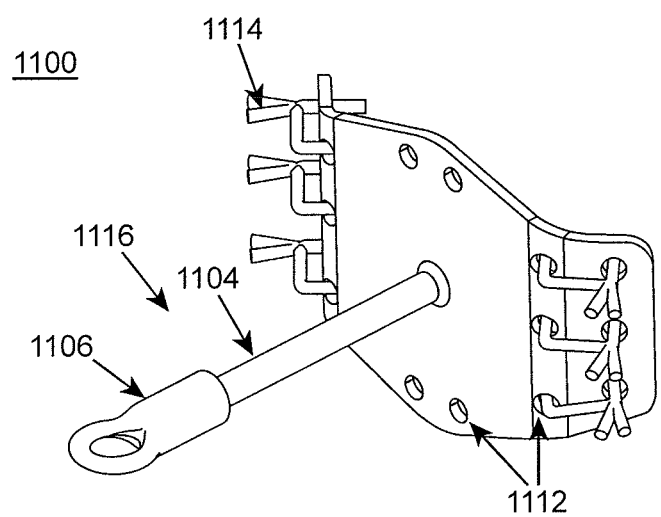

FIGS. 11A and 11B show a device 1100, according to an embodiment of the invention. In some embodiments, the device 1100 is constructed from multiple components, which can include a base 1102 plate and first post portion 1104 extending therefrom and a detachably coupled second post portion 1106. The first post portion 1104 can be constructed from titanium and welded to the base plate 1102. The first post portion 1104 and the base plate 1102 can be constructed from other biologically compatible materials as well, such as treated aluminum alloys, certain polymers, and include micro-coatings or surface treatments to encourage a positive long-term tissue reaction. The materials used for the device 1100 are preferably MR compatible and/or MR safe. The base plate 1102 and first post portion 1104 can be machined as one piece from solid titanium billet (commercially pure or nearly pure), die cast, 3D-printed, or, as shown, assembled together from multiple parts. The titanium material used can meet ASTM specification F-67-06 for Grade 2.

A distal end 1108 of the first post portion 1104 can be laser welded to the base plate to form a permanent coupling therebetween. A proximal end 1110 of the first post portion 1104 can be pointed and include threads to detachably couple to the second post portion 1106. In other embodiments, the first post portion 1104 can have a rounded or blunt proximal end.

The second post portion 1106 is constructed as a brass eye-hook. The second post portion 1106 can be constructed from a non-biologically compatible material, since it is not intended to contact internal tissue. However, care should be taken to avoid choosing materials which impart a galvanic reaction between the first post portion 1104 and the second post portion 1106. The second post portion 1106 can include threads to detachably couple to the first post portion 1104. However, other coupling junctions can be use, such as a quick release ball and spring junction, an interference fit, or a quarter-turn fitting. Many other common coupling junctions can be used, as is known in the art.

In some embodiments, the base plate 1102 can have a width of approximately 30 mm and a height of approximately 20 mm. The plate 1102 is shown to include two bends for fitting against the curvature of the cricoid cartilage. In other embodiments, a fully curved shape or fully flat shape is also possible depending on a patient's particular anatomy. In other embodiments, the plate 1102 can be constructed from a malleable material and/or provided with preferential zones of bending, such as slits or a line of holes, to enable a surgeon to shape the plate 1102 in the field of use using only hands or simple tools.

As shown in FIG. 11B, the base plate 1102 can include a plurality of peripheral holes 1112 to enable sutures 1114 to pass through. The placement of the peripheral holes 1112 also can enable attachment of the base plate 1102 to an anterior ring of a patient's cricoid cartilage C.

As further shown in FIG. 11B, the first post portion 1104 couples to the second post portion 1106 to form an assembled post 1116. In some embodiments, the assembled post 1112 extends from the plate 1102 at a height of approximately 25 mm from the bottom-most portion of the plate.

It should be understood that the dimensions given herein are exemplary and can vary per patient depending on the amount of subcutaneous fat present and/or skin thickness. In some embodiments, a suite of different assembled post lengths are available to a surgeon for attachment to the plate prior to implantation.

In use, after implantation into a patient, the second post portion 1106 screws onto the distal end of the first post portion 1102 to protect the patient from the proximal end 1110 of the device and allow the patient to conceal the device 1100 by attaching it to a necklace for cosmetics, or lanyard. As shown, the second post portion 1106 threads onto the exterior of the first post portion 1104 for attachment thereto. In other embodiments, the second post portion 1104 can thread into a hollow portion of the first post portion 1106. In some embodiments, the second post portion 1104 can take other forms, such as a cap with a hole, a clasp, or a T-bar.

Figure 11C:
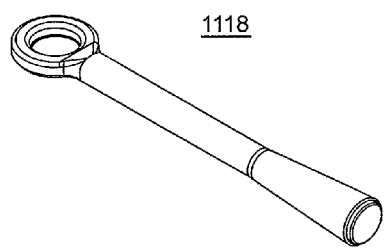
FIG. 11C shows a one-piece post, according to an embodiment of the invention.

FIG. 11C shows a one-piece post 1118, according to an alternative embodiment of the invention. The one-piece post 1118 does not have the two-piece construction of the assembled post 1110. The one-piece post 1118 can be formed from a biologically compatible material, as described herein, since internal tissue contact is required.

Figure 11D:
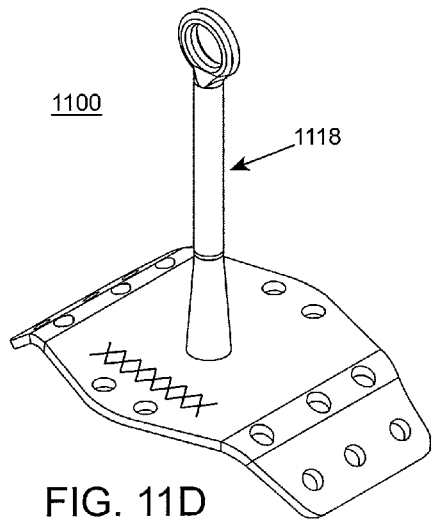
FIG. 11D shows a perspective view of a device having a one-piece post, according to an embodiment of the invention.

FIG. 11D shows the device 1100, according to an alternative embodiment of the invention. Here, a one-piece post 1118 is provided with the base plate 1120. In use, the patient operates the device 1100 as described herein, however, here there is no risk of losing parts.

Figure 11E:
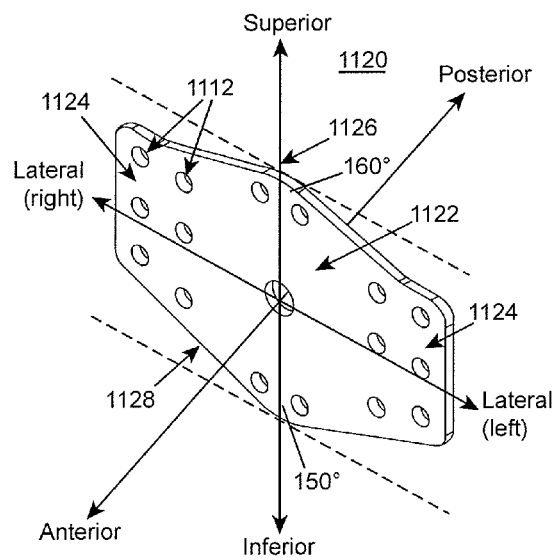
FIGS. 11E and 11F respectively show perspective views of a pre-assembled base-plate and a formed base-plate, according to embodiments of the invention.
Figure 11F:
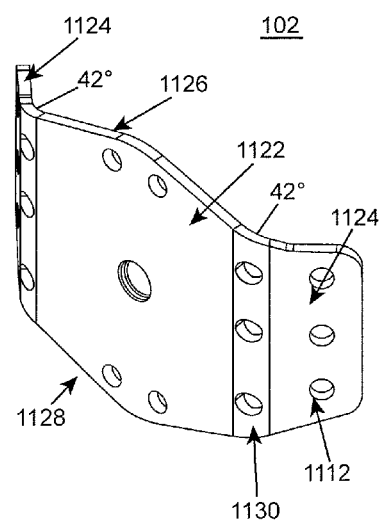

FIGS. 11E and 11F respectively show a pre-assembled base plate 1120 and the finally formed base-plate 1102. Here, the base plate 1120 is substantially planar, as compared to base plate 1102. The base plate 1120 can be formed to take the shape of base plate 1102, via a bending apparatus, or provided as shown with the device 1100 (assembled with first post portion 1104 or the one-piece post 1115) to enable field bending. The pre-assembled base-plate can be dimensioned to have a lateral width of approximately 25 mm, and a height of approximately 20 mm.

The base plate 1120 includes a central portion 1122, which can be planar or curved. Two winged portions 1124 extend laterally from the central portion 1122, can be angled in the posterior direction at approximately 42°. A superior edge 1126 can be obtusely angled facing the inferior direction at approximately 160°, and an inferior edge 1128 can be obtusely angled facing the superior direction at approximately 150°. Arrays of holes 1112 can be placed on the winged portions 1124 and at superior and inferior most sides of the base plate 1120 and in a curved bending zone 1130 between the central portion 1122 and the winged portions 1124. This configuration is an example of a base-plate 1120 that is sized, shaped, and contoured to enable attachment to an anterior ring of a patient's cricoid cartilage C, to properly enable force transfer, and thus articulate with the patient's cricoid cartilage C after attachment.

Figure 12:
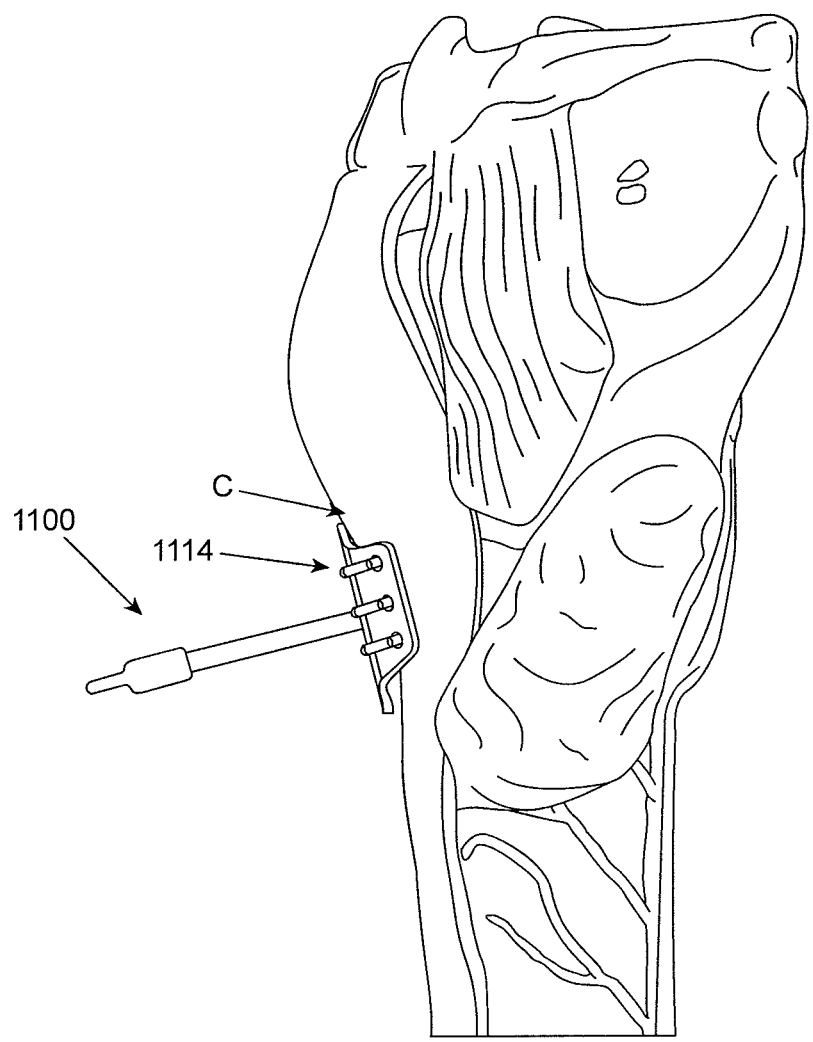
FIG. 12 shows a side view of the device of FIGS. 11A and 11B implanted into a patient, according to one embodiment of the invention.

FIG. 12 shows the device 1100 is implanted within a patient, according to an embodiment of the invention. Generally, a 2 cm incision can be made in a cosmetically appealing skin crease 3 cm below the level of the cricoid cartilage C. The strap muscles can be then divided according to a midline and moved to expose the cricoid cartilage C. The device 1100 can then be secured to the cricoid cartilage C with a plurality of 2-0 Nylon sutures, for example, 5 or more, although other sizes may be used as well as wire. As shown, sutures 1114 loop through the holes on the base plate 1102 in order to secure the base plate 1102 to tissue. The post will be brought out through the skin at the level of the cricoid cartilage C. The strap muscles can then be re-approximated in the midline and the skin closed in two layers.

In use, the patient can grasp the post using hand-force, and/or the eye-hook or a lanyard attached to the eye-hook, when the patient is required to swallow food or drink liquid. Pulling the post away from the trachea will accordingly pull the cricoid cartilage C, and open the upper sphincter of the esophagus. No other actuation by an external device, such as a mechanically operated magnetic device or motorized device, is required. In some embodiments, the patient can attach a small weight (e.g., 3-6 lbs) to the lanyard to keep the upper sphincter continuously open during a meal. Accordingly, use of the device can allow a patient with OPD to eat and drink. In other embodiments, a simple device can be attached to the post which maintains the opening of the upper sphincter, for example, by applying a biasing counter-force to the neck skin.

Figure 13A:
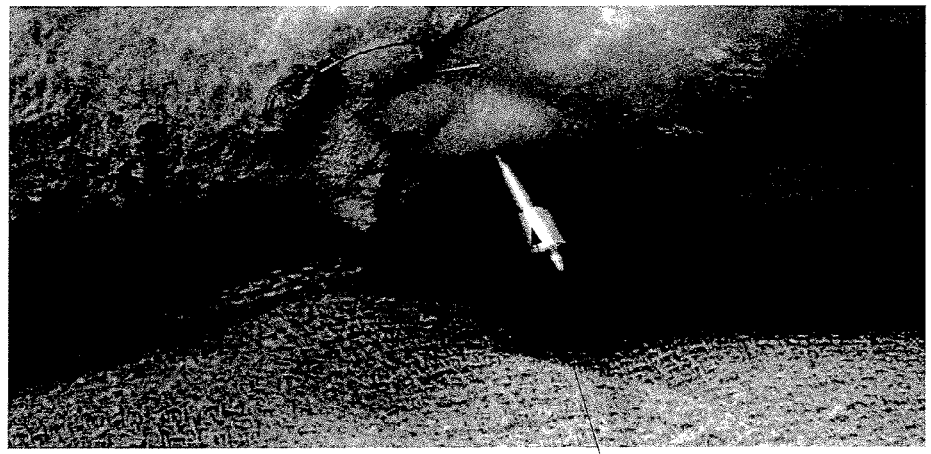
FIG. 13A shows an image of the cervical skin of a sheep immediately after implantation of the device of FIGS. 1A and 1B.
Figure 13B:
FIG. 13B shows an image of the device of FIGS. 11A and 11B five weeks after sheep implantation.

Post Device Animal Study:

FIG. 13A shows an image of the cervical skin of a sheep immediately after device implantation. FIG. 13B shows the device 1100 five weeks after sheep implantation. There were no signs of infection or inflammation.

Figure 13C:
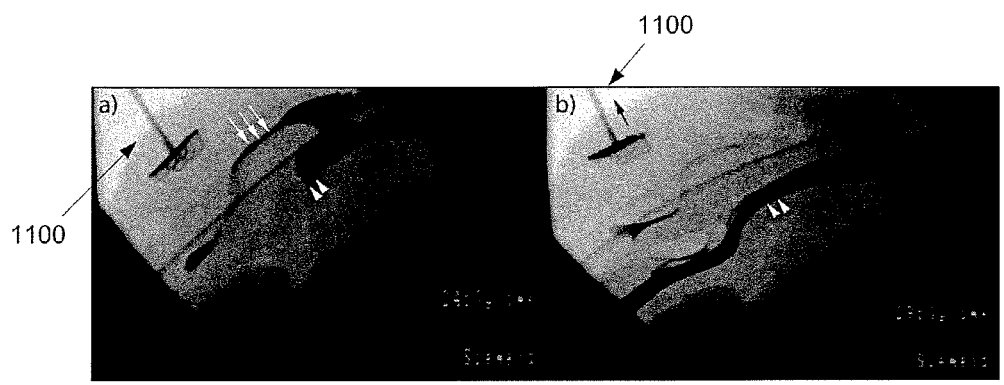
FIG. 13C shows fluoroscopic images of the device of FIGS. 11A and 11B in use in an ovine model of oropharyngeal dysphagia.

FIG. 13C shows a fluoroscopic swallow study in an ovine model of oropharyngeal dysphagia. Barium was instilled into the hypopharynx of the sheep. The upper esophageal sphincter is closed (white arrowheads) and there is gross aspiration into the trachea (white arrows). The device 1100 is pulled forward (black arrow). The upper esophageal sphincter opens to super-physiologic proportions (white arrowheads) and the aspiration is eliminated.

The device 1100 was removed four months after device implantation. There was a capsule around the device displaying high biocompatibility. There was no gross or histologic evidence of cartilage damage after 40,000 pulls on the implanted device 1100. The device 1100 opened the upper esophageal sphincter to a super-physiologic dimension. The device 1100 eliminated 100% of aspiration.

Figures 13D, 13E:
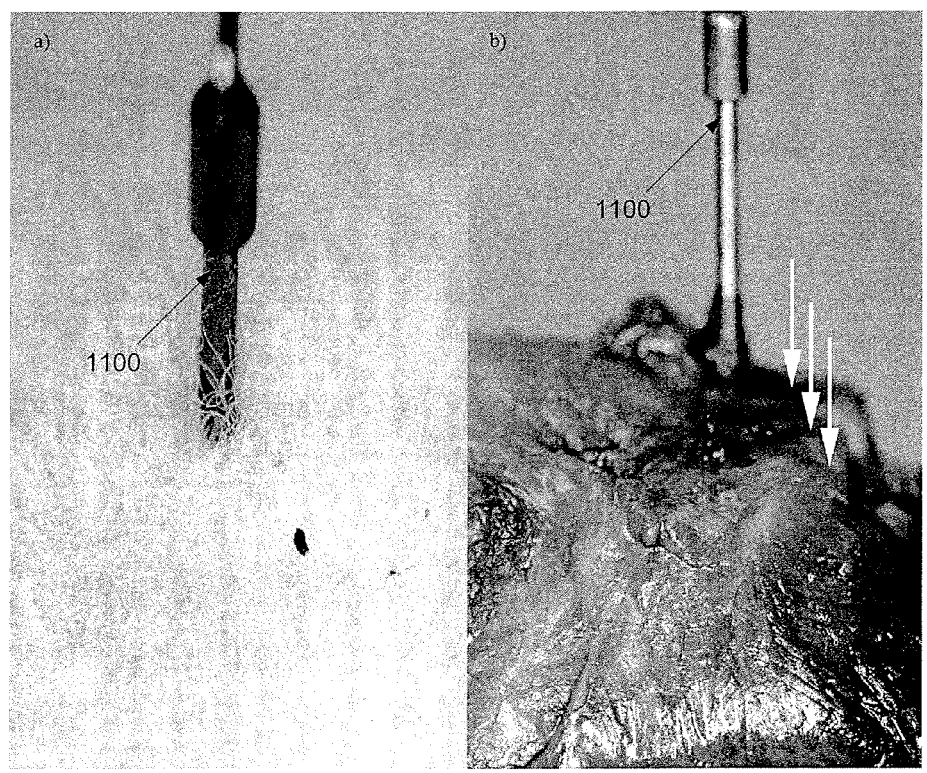
FIGS. 13D and 13E show the device of FIGS. 11A and 11B four months after sheep implantation.

FIGS. 13D and 13E shows the device as placed in a sheep four months after device implantation. FIG. 13D shows cervical skin around the post after shearing of the animal. There was no sign of any irritation or infection. FIG. 13E shows a thick fibrous capsule (white arrows) that developed around the implant at the time of device explantation. There was no evidence of damage, irritation, or rejection.

The above description is illustrative and is not restrictive. Many variations of the invention will become apparent to those skilled in the art upon review of the disclosure. The scope of the invention should, therefore, be determined not with reference to the above description, but instead should be determined with reference to the claims along with their full scope or equivalents.

One or more features from any embodiment may be combined with one or more features of any other embodiment without departing from the scope of the invention.

A recitation of "a", "an" or "the" is intended to mean "one or more" unless specifically indicated to the contrary.

What is claimed is:

1. A device for opening a passageway of a patient, the device comprising:
 a base plate configured to attach to an anterior ring of the patient's cricoid cartilage, and articulate with the patient's cricoid cartilage after attachment thereto; and a post extending from said base plate in an anterior direction, the post being of a sufficient length to protrude through a patient's skin when the base plate is attached to the anterior ring of the patient's cricoid cartilage, the post being further configured with a proximal end to impart a pulling force to the base plate to move the base plate and attached cricoid cartilage and thereby affect opening of the upper sphincter of the esophagus, wherein the base plate and post are non-magnetic, and wherein the base plate is formed to curve away from the post towards a posterior direction such that the base plate has a concave posterior facing surface, wherein the post comprises a first post portion and a second post portion, wherein a distal end of the first post portion is affixed to the base plate and wherein a proximal end of the first post portion is configured to detachably couple to the second post portion.

2. The device of claim 1 wherein a distal portion of the second post portion is threaded for detachably coupling to the first post portion.

3. The device of claim 1, wherein the base plate is shaped to match a profile of the cricoid cartilage of the patient.

4. The device of claim 1, wherein the proximal end of the post comprises a ring.

5. The device of claim 4, wherein a lanyard is attached to the ring.

6. The device of claim 1, wherein the base plate comprises a planar base portion and two lateral wing portions angled towards the posterior direction.

7. The device of claim 6, wherein the base plate includes a superior edge obtusely angled towards an inferior direction.

8. The device of claim 7, wherein the base plate includes an inferior edge obtusely angled towards a superior direction.

9. The device of claim 1, wherein the device is non-motorized.

10. The device of claim 1, wherein the device is MR compatible or MR safe.

11. The device of claim 10, wherein the post and base plate are constructed from titanium.

12. The device of claim 1, wherein the base plate comprises a plurality of passages for suturing the base plate to the anterior ring of the patient's cricoid cartilage.

13. A method for surgically installing a device into a patient, the method comprising:

obtaining a device comprising:
- a base plate configured to attach to an anterior ring of the patient's cricoid cartilage, and articulate with the patient's cricoid cartilage after attachment thereto; and
- a post extending from the base plate, the post being of a sufficient length to protrude through a patient's skin when the base plate is attached to the anterior ring of the patient's cricoid cartilage, the post being further configured with a proximal end to impart a pulling force to the base plate to move the base plate and attached cricoid cartilage and thereby affect opening of the upper sphincter of the esophagus;

creating an incision below the cricoid cartilage of the patient;

dividing strap muscles according to a midline;

moving the strap muscles to expose the cricoid cartilage;

attaching the base plate to the cricoid cartilage with sutures;

positioning a first portion of the post to extend outside of the skin of the patient;

repositioning the divided strap muscles about the midline; and closing the incision.

* * * * *